(12) United States Patent
Morgan (10) Patent No.: US 8,361,992 B2
(45) Date of Patent: Jan. 29, 2013

(54) COMPLEXES OF 4-HYDROPEROXY IFOSFAMIDE AS ANTI-TUMOR AGENTS

(75) Inventor: Lee Roy Morgan, New Orleans, LA (US)

(73) Assignee: Dekk-Tec, Inc., New Orleans, LA (US)

( * ) Notice: Subject to any disclaimer, the term of this patent is extended or adjusted under 35 U.S.C. 154(b) by 0 days.

(21) Appl. No.: 13/202,833

(22) PCT Filed: Feb. 24, 2010

(86) PCT No.: PCT/US2010/025252
§ 371 (c)(1),
(2), (4) Date: Aug. 23, 2011

(87) PCT Pub. No.: WO2010/099213
PCT Pub. Date: Sep. 2, 2010

(65) Prior Publication Data
US 2011/0319365 A1    Dec. 29, 2011

Related U.S. Application Data

(60) Provisional application No. 61/155,072, filed on Feb. 24, 2009.

(51) Int. Cl.
C07F 9/6584   (2006.01)
A61K 31/675   (2006.01)
A61P 35/00    (2006.01)
A61P 35/02    (2006.01)

(52) U.S. Cl. .......................................... 514/89; 558/81
(58) Field of Classification Search .......... 558/81; 514/89
See application file for complete search history.

(56) References Cited

FOREIGN PATENT DOCUMENTS
GB  1421559       1/1976
GB  1421559 A  *  1/1976
WO  WO 2006/047575  5/2006

OTHER PUBLICATIONS

Stahl et al. Handbook of Pharmaceutical Salts Properties, Selection and Use, published on May 14, 2008, (29 pages).*
Hohorst et al., "Synthesis of 4-Hydroperoxy Derivatives of Ifosfamide and Trofosfamide by Direct Ozonation and Preliminary Antitumor Evaluation in Vivo," *Cancer Res.* 36:2278-2281, 1976.
Styczynski et al., "In Vitro Activity of Oxazaphosphorines in Childhood Acute Leukemia: Preliminary report," *Acta Biochimica Polonica*, vol. 49, pp. 221-225, 2002.
Styczynski et al., "In Vitro Activity of Glufosfamide in Childhood Acute Leukemia," *Anticancer Research*, vol. 22, pp. 247-250, 2002.

* cited by examiner

*Primary Examiner* — Kahsay T Habte
(74) *Attorney, Agent, or Firm* — Klarquist Sparkman, LLP.

(57) ABSTRACT

The present disclosure concerns complexes of 4-hydroperoxy ifosfamide. In one embodiment the complexes can be represented by the formula

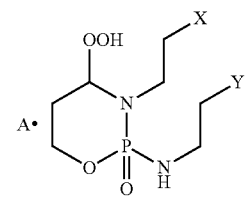

wherein A represents an ammonium species selected from the conjugate acid of a basic amino acid, quaternary ammonium, aliphatic ammonium, heterocyclic ammonium, aromatic ammonium, substituted and unsubstituted pyridinium, guanidinium, and amidinium, and wherein X and Y independently represent leaving groups. Also disclosed herein are methods for making such compounds and formulating pharmaceutical compositions thereof. Methods for administering the disclosed compounds to subjects, particularly to treat hyperproliferative disorders, also are disclosed.

25 Claims, 4 Drawing Sheets

COMPLEXES OF 4-HYDROPEROXY IFOSFAMIDE AS ANTI-TUMOR AGENTS

CROSS REFERENCE TO RELATED APPLICATION

This is the U.S. National Stage of International Application No. PCT/US2010/025252, filed Feb. 24, 2010, which was published in English under PCT Article 21(2), which in turn claims the benefit of U.S. Provisional Application No. 61/155,072, filed Feb. 24, 2009, which is incorporated by reference herein in its entirety.

ACKNOWLEDGMENT OF GOVERNMENT SUPPORT

This invention was made with government support under National Institutes of Health Grant #CA94566. The government has certain rights in the invention.

FIELD

This disclosure concerns complexes of 4-hydroperoxy ifosfamide. Also disclosed are pharmaceutical compositions and methods for using such compositions to treat hyperproliferative disorders.

BACKGROUND

Cyclophosphamide (CPA) is the most widely used agent of the alkylating agent class in the clinical treatment of cancer. Two congeners, ifosfamide (IFOS, Holoxan®) and trofosfamide (Trofos, Ixoten®) are also in clinical use. CPA is still advantageous in the clinical treatment of lymphoma and breast cancer, while IFOS is effective in the clinical treatment of testicular cancer and soft tissue sarcomas and is also being used in the clinical treatment of breast cancer in the ICE (IFOS, carboplatin, etoposide) regimen. Patients with CPA-resistant breast cancer have responded to a doxorubicin-isophosphoramide mustard (IPM) based treatment, indicating the possibility of some lack of cross resistance between CPA and IPM may exist. In addition, clinical trials with IFOS for treatment of sarcoma, lymphoma and small cell lung cancers have shown an apparent lack of cross-resistance with CPA.

IFOS is converted by an activation pathway initiated by hepatic microsomes to 4-HO-IFOS, which spontaneously undergoes opening of the oxazaphosphorine ring to produce aldo-IFOS, which in turn eliminates acrolein spontaneously and/or possibly through serum albumin catalysis, generating the active metabolite, IPM. IFOS differs from CPA particularly in its metabolic dechloroethylation to produce chloroacetaldehyde. CPA generates minimal chloroacetaldehyde. Acrolein has been implicated in the dose limiting toxicity (hemorrhagic cystitis and secondary tumor promotion) noted with both IFOS and CPA.

The 4-hydroperoxide of IFOS (4-hydroperoxy IFOS; 4-HOOI) is a pre-activated form of 4-hydroxyl-IFOS, the initial hepatic metabolite of IFOS. Unfortunately 4-HOOI is too unstable to be manufactured and used for human treatment.

SUMMARY

The present disclosure provides complexes of 4-HOOI which are stable and can be utilized for treatment, for example for a mammalian subject. Unlike IFOS, 4-HOOI does not require hepatic microsomal activation, is readily absorbed by cancer cells and releases IPM and acrolein in situ, and not in the systemic circulation. As a result, 4-HOOI provides significant anti-tumor activity, with reduced toxicity as compared to IFOS and CPA.

Disclosed herein are compounds of the formula:

wherein A represents an ammonium species selected from the conjugate acid of a basic amino acid, quaternary ammonium, aliphatic ammonium, heterocyclic ammonium, aromatic ammonium, substituted and unsubstituted pyridinium, guanidinium, and amidinium, and wherein X and Y independently represent leaving groups. In particular examples, the complex includes the conjugate acid of a basic amino acid, such as lysine, homolysine, arginine, homoarginine, histidine, ornithine, or a combination of two or more thereof. In one specific example, the complex includes the conjugate acid of lysine.

In one embodiment, pharmaceutical compositions are disclosed that include one or more of the compounds described above. In some examples, the compositions can include one or more therapeutic agents other than those described by the formula above for use in combination therapy.

Also disclosed herein are a lyophilisate and a method for producing a lyophilisate including the disclosed 4-HOOI complexes. In certain embodiments, the method includes contacting 4-HOOI and an amine (such as lysine or tris(hydroxymethyl)aminomethane (Tris)) with water and lyophilizing the resulting mixture. In certain embodiments, the mixture and the resulting lyophilisate include an excipient, such as mannitol, anhydrous lactose, sucrose, D(+)-trehalose, dextran 40 or povidone (PVP K24).

In some embodiments, methods for treating mammalian subjects, such as human subjects, having hyperproliferative disorders using the disclosed 4-HOOI complexes are disclosed. In some examples, the hyperproliferative disorder includes a central nervous system (CNS) tumor (for example, a primary or metastatic brain tumor), such as a glioblastoma, astrocytoma, or ependymoblastoma. In other examples, the hyperproliferative disorder includes breast cancer, lung cancer, ovarian cancer, osteosarcoma, or leukemia. Such methods can employ one or more of the compounds and compositions described above.

It has surprisingly been found that 4-HOOI efficiently passes through the blood brain barrier and concentrates in CNS tumors without accumulating in normal brain tissue. This surprising ability of 4-HOOI (including the complexes disclosed herein) to selectively concentrate in such tumors provides a treatment for brain and other CNS tumors that can achieve high concentrations of drug in the target tissue while substantially sparing normal tissue from damage. This favorable therapeutic index permits higher doses of the drug to be used than would otherwise be possible with a less selective agent.

The foregoing and other features will become more apparent from the following detailed description, which proceeds with reference to the accompanying figures.

DETAILED DESCRIPTION

I. Abbreviations

4-HOOI: 4-hydroperoxy ifosfamide
ACR: acrolein
CAA: chloroacetaldehyde
CPA: cyclophosphamide
DLT: dose-limiting toxicity
IFOS: ifosfamide
IPM: isophosphoramide mustard
LTS: long-term survival
MTD: maximum tolerated dose

II. Terms

Unless otherwise noted, technical terms are used according to conventional usage. The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

All publications, patent applications, patents, and other references mentioned herein are incorporated by reference in their entirety for all purposes. In case of conflict, the present specification, including explanations of terms, will control. Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

4-Hydroperoxyifosfamide (4-HOOI): A compound having the structure:

wherein X and Y independently represent leaving groups, for example halogens or sulfonates. In some examples, X and Y are each Cl. 4-HOOI is a pre-activated form of 4-hydroxyl-IFOS, which is the initial hepatic metabolite of IFOS.

Aliphatic amine: A compound of the formula $NR_1R_2R_3$, wherein at least one of $R_{1-3}$ is an aliphatic group. The term "acyclic aliphatic amine" refers to an aliphatic amine, wherein at least one of the aliphatic groups is acyclic. The term "heterocyclic amine" refers to a compound of the formula $NR_1R_2R_3$, wherein at least one of $R_{1-3}$ is a heterocyclic group or $R_1$, $R_2$ and/or $R_3$ taken together with their common nitrogen atom form a ring.

Amino acid: Refers to both natural and unnatural amino acids, including α-amino acids, in their D and L stereoisomers for chiral amino acids. Examples of basic amino acid residues include those having a basic side chain, such as an amino or guanidino group. Basic amino acid residues include, without limitation, arginine, histidine, homoarginine, lysine, homolysine, and ornithine.

Hyperproliferative disorder: Any of a number of diseases that are characterized by uncontrolled, abnormal proliferation of cells, the ability of affected cells to spread locally or through the bloodstream and lymphatic system to other parts of the body (for example, metastasize) as well as any of a number of characteristic structural and/or molecular features. In some examples, a hyperproliferative disorder includes a tumor (such as a benign or malignant tumor).

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic agents, such as one or more of the disclosed 4-HOOI complexes.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol, or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Subject: Living multi-cellular vertebrate organism, a category that includes human and non-human mammals.

Therapeutically effective amount: A dose sufficient to prevent advancement, delay progression, or to cause regression of a disease, or which is capable of reducing symptoms caused by the disease, such as cancer, for example a central nervous system cancer.

Tumor: A neoplasm that may be either malignant or non-malignant (benign). Tumors of the same tissue type are tumors originating in a particular organ (such as brain, breast, lung, or colon) or cell type (such as glial cell, for example astrocyte or oligodendrocyte). Tumors include original (primary) tumors, recurrent tumors, and metastases (secondary tumors). A tumor recurrence is the return of a tumor, at the same site (for example, in the same organ or tissue) as the original (primary) tumor, after the tumor has been removed surgically, by drug or other treatment, or has otherwise disappeared. A metastasis is the spread of a tumor from one part of the body to another. Tumors formed from cells that have spread are called secondary tumors (or metastatic tumors) and contain cells that are like those in the original (primary) tumor. There can be a recurrence of either a primary tumor or a metastasis.

III. Complexes of 4-Hydroperoxy Ifosfamide

The compounds and compositions disclosed herein include 4-hydroperoxy ifosfamide (4-HOOI) that is formulated with one or more equivalents of a base. Because 4-HOOI is acid labile and is acidic, the presently disclosed compounds offer greater stability as well as other advantages. The advantages of the disclosed formulations in terms of synthesis, stability and bioavailability will be apparent to those of ordinary skill in the art upon consideration of the present disclosure.

The compounds disclosed herein include complexes of 4-HOOI, for example, including one or more cations or other conjugate species (such as a hydrogen bonding species). In one embodiment, the cations can be a conjugate acid of an amine base or can be a quaternary ammonium cation.

In some examples, the disclosed compounds include complexes of 4-HOOI, including compounds having the formula:

wherein A represents an ammonium species selected from the conjugate acid of a basic amino acid (such as lysine, homolysine, arginine, homoarginine, histidine, or ornithine), quaternary ammonium, aliphatic amine, heterocyclic amine, aromatic amine, substituted and unsubstituted pyridine, guanidine, and amidine, and wherein X and Y independently represent leaving groups. In some examples, X and Y are independently halogen. In a particular example, X and Y are the same, for example X and Y are both Cl.

Without being bound by theory, it is believed that in some embodiments the disclosed complexes are formed via hydrogen bonding of the ammonium species (for example a basic amino acid) with 4-HOOI. However, in some examples, the disclosed complexes may be salts of 4-HOOI.

Suitable ammonium species include the conjugate acids (as used herein terms that refer to amines should be understood to include their conjugate acids unless the context clearly indicates that the free amine is intended) of bases including basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium are examples of suitable ammonium species that can be used.

In particular examples, the complex includes the conjugate acid of a basic amino acid, such as lysine, homolysine, arginine, homoarginine, histidine, ornithine, or a combination of two or more thereof. In one specific example, the complex includes the conjugate acid of lysine. In some examples, the complex includes a 1:1 ratio of lysine and 4-HOOI. In other examples, the complex includes a 2:1 ratio of lysine and 4-HOOI. In some examples, the melting point of the complex is greater than about 275° C.

Additional examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tris(hydroxymethyl)aminomethane (Tris), tri-(2-hydroxyethyl)amine and N-methyl-D-glucamine. Another suitable amine base includes cyclohexylamine.

In particular examples, the complex (such as a complex of a 1:1 or 2:1 ratio of lysine and 4-HOOI) is at least about 80% pure, at least about 85% pure, at least 90% pure, at least 95% pure, at least 97% pure, at least 98% pure, or even at least 99% pure. In some examples, no single impurity exceeds 1% by weight. In some examples, purity is measured relative to all other components of the composition, while in other examples (e.g., where the compound is part of a pharmaceutical composition or lyophilisate mixture), purity may be measured relative to degradation products of the compound or by-products of the manufacture of the compound, thereby excluding other components purposefully added to the composition.

In some examples, A represents $BH^+$ and B is an amine selected from the basic amino acids (for example, lysine, homolysine, arginine, homoarginine, histidine, or ornithine), cyclohexylamine, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine.

In certain embodiments, the complexes described above can include a second amine or ammonium group. In some examples, the compounds disclosed herein include more than one equivalent of an amine for each equivalent of 4-HOOI. Such embodiments include those having non-integer ratios of amine to 4-HOOI. In some examples, the compounds have a two to one, three to one ratio, or more of amine to 4-HOOI. In some examples, the disclosed complexes include two equivalents of amine base (for example, lysine) per equivalent of 4-HOOI.

In other examples, an amine base used to form 4-HOOI complexes includes more than one amino group; such bases can be termed "multibasic." More specifically, certain examples of multibasic bases that can be used have two amino groups; such compounds can be referred to as "dibasic." For example, one suitable dibasic molecule is N,N-dimethylaminopyridine, which includes two basic amino groups. In a one example, a compound disclosed herein includes 4-HOOI and one equivalent of a dibasic amine.

In some examples the disclosed compounds include one or more zwitterionic bases. Examples of such bases include basic amino acids, which are zwitterionic at physiological pH. Examples of zwitterionic bases, including amino acids, have additional functional groups that can function as hydrogen bond donors and/or acceptors to stabilize 4-HOOI.

Without being bound by theory, it is believed that the disclosed complexes stabilize 4-HOOI in the presence of water and prevent ring opening and release of IPM, which decomposes. In some examples, the compounds are 4-HOOI complexes, wherein the complex has a half-life at room temperature (for example, about 22-25° C.) in the presence of water that is greater than a half-life of 4-HOOI (for example, as the free peroxide) in the presence of water under the same conditions. In particular examples, a 4-HOOI complex has a half-life in the presence of water that is equal to or greater than twice as long as 4-HOOI itself in the presence of water, more preferably, equal to or greater than five times. In some examples, the compounds are 4-HOOI complexes (such as 4-HOOI.Lys), wherein the complexes are stable at room temperature in the presence of water for at least 15 minutes, 30 minutes, 60 minutes, 90 minutes, 2 hours, 3 hours, 4 hours, 6 hours, 8 hours, 12 hours, 16 hours, one day, two days, three days, four days, five days, six days, one week, or more.

As used herein, the term "stable" means that the purity of the 4-HOOI complex (such as a lyophilisate) after a period of time (for example, at least one day, one week, two weeks, one month, two months, three months, six months, 8 months, 10 months, one year, or more) is at least 90%, at least 95%, at least 97%, or even at least 99% of the initial purity, which may be determined for example, by HPLC or GC-MS, as described in Example 1, below.

In some examples, the 4-HOOI complex has advantageous solubility characteristics. For example, in some examples, the disclosed 4-HOOI complexes (such as 4-HOOI.Lys complexes) are at least as soluble in aqueous solvents as 4-HOOI. In other examples, the 4-HOOI complex has improved solubility in aqueous solvents as compared to 4-HOOI.

One embodiment of the present disclosure concerns antihyperproliferative agents of the formula:

With reference to the formula, B can be, for each n, an independently selected basic molecule. In one example of the formula, B can be selected from the basic amino acids (such as lysine, homolysine, arginine, homoarginine, histidine, or ornithine), acyclic aliphatic amines, di- and tri alkyl amines, heterocyclic aliphatic amines, aromatic amines, substituted and unsubstituted pyridines, cyclic and acyclic guanidines, and cyclic and acyclic amidines. Typically, n is from 1 to about 3 such that the formula can include different basic molecules, or 2 or more of the same basic molecule. With continued reference to the formula, X and Y are leaving groups (for example, halogen (such as Cl or Br) or sulfonate). A person of ordinary skill in the art will understand that the illustrated structure includes an acidic proton, and as such exists predominantly as its conjugate base at physiological pH and in the presence of a base such as B. Likewise, B, being a basic group exists predominantly as its conjugate acid at physiological pH and in the presence of 4-HOOI. Exemplary compounds of the disclosure are depicted in Table 1.

TABLE 1

Exemplary 4-HOOI complexes

| B | n | X | Y |
|---|---|---|---|
| lysine | 2 | Cl | Cl |
| NH$_3$ | 2 | Cl | Cl |
| cyclohexylamine | 2 | Cl | Cl |

TABLE 1-continued

| | | | |
|---|---|---|---|
| N-methyl-D-glucamine | 2 | Cl | Cl |
| N,N-dimethylaminopyridine | 1 | Cl | Cl |
| arginine | 2 | Cl | Cl |
| lysine | 2 | Cl | —SO$_2$CH$_3$ |
| lysine | 2 | Br | —SO$_2$CH$_3$ |
| tris(hydroxymethyl)aminomethane | 1 | Cl | Cl |

In one embodiment, the compounds disclosed herein include a metal cation, such as an alkali metal cation. Examples of such cations include Li$^+$, Na$^+$, K$^+$ and Rb$^+$ and Cs$^+$.

IV. Compositions and Methods

Another aspect of the disclosure includes pharmaceutical compositions, such as sterile pharmaceutical compositions, prepared for administration to a subject (for example, a mammalian subject, such as a human) and which include a therapeutically effective amount of one or more of the currently disclosed compounds or a lyophilisate of one or more of the disclosed compounds. Such sterile compositions may be prepared by passing a solution of the 4-HOOI complexes disclosed herein through a sterile antimicrobial filter.

Also disclosed herein are lyophilisates that include 4-HOOI formulated with one or more equivalents of a base. Because 4-HOOI is acid labile and acidic, the presently disclosed lyophilisates offer greater stability as well as other advantages. The advantages of the disclosed formulations in terms of synthesis, stability and bioavailability will be apparent to those of ordinary skill in the art upon consideration of the present disclosure. Additional advantages of 4-HOOI formulated with one or more equivalents of a base may include increased solubility in water or bodily fluids. In some examples, lyophilisates that include 4-HOOI may be prepared by contacting 4-HOOI with at least one equivalent of an amine base (such as basic amino acids, aliphatic amines, heterocyclic amines, aromatic amines, substituted and unsubstituted pyridines, guanidines, or amidines) in the presence of water and lyophilizing the resulting mixture.

In certain embodiments, the disclosed lyophilisates are complexes of 4-HOOI including one or more base. In some examples, the base can be a conjugate acid of an amine base or can be a quaternary ammonium cation. Suitable bases for 4-HOOI include the conjugate acids (as used herein terms that refer to amines should be understood to include their conjugate acids unless the context clearly indicates that the free amine is intended) of bases including basic amino acids (such as lysine, homolysine, arginine, homoarginine, histidine, or ornithine), aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium are examples of suitable ammonium species that can be used. In other examples, such a lyophilisate may further include an excipient. Suitable excipients include, but are not limited to, mannitol, anhydrous lactose, sucrose, D(+)-trehalose, dextran 40 and povidone (PVP K24).

In some examples, the compounds and compositions, such as the lyophilisates disclosed herein, are stable at room temperature for at least one week, at least two weeks, at least three weeks, at least one month, at least two months, at least three months, or even at least six months. In other examples, the complexes are stable at lower temperatures (e.g., between about 0° C. and about 20° C., between about 0° C. and about 10° C., or even between about 2° C. and about 8° C.) for at least one week, at least two weeks, at least three weeks, at least a month, at least two months, at least three months, at least four months, or even at least six months. In certain embodiments, the lyophilisate comprises a 4-HOOI complex. In particular examples, the lyophilisate comprises 4-HOOI.Lys.

In further examples, the complexes described above can include a second amine or ammonium group. In one example, the lyophilisates disclosed herein include more than one equivalent of an amine for each equivalent of 4-HOOI. Such examples include those having non-integer ratios of amine to 4-HOOI. In certain embodiments, the lyophilisates have a two to one or three to one ratio of amine to 4-HOOI. In one example, the disclosed complexes include two equivalents of amine base per equivalent of 4-HOOI. In some examples, an amine base used to form 4-HOOI complexes includes more than one amino group; such bases can be termed "multibasic." More specifically, certain examples of multibasic bases that can be used have two amino groups; such compounds can be referred to as "dibasic." For example, one suitable dibasic molecule is N,N-dimethylaminopyridine, which includes two basic amino groups. Certain examples of a lyophilisate disclosed herein include 4-HOOI and one equivalent of a dibasic amine.

In particular examples, lyophilisates of disclosed 4-HOOI complexes improve the reconstitutional stability as compared to a lyophilized preparation of 4-HOOI itself. In certain such embodiments, a lyophilisate prepared from disclosed complexes of 4-HOOI, such as from 4-HOOI and lysine, optionally including an excipient, for example, a bulking agent, such as mannitol, that has been reconstituted in an aqueous solution (such as 5% sodium chloride) maintains >90% potency for at least about 30 minutes, 60 minutes, 90 minutes, 120 minutes, 140 minutes, or even at least about 160 minutes.

In some examples, dissolving a complex of 4-HOOI, such as 4-HOOI.Lys, or a lyophilisate prepared from a 4-HOOI complex, such as 4-HOOI.Lys, and an optional excipient, for example, a bulking agent, such as mannitol, in an aqueous solution maintains at least 96%, at least 97%, at least 98%, or even at least 99% purity for at least about 30 minutes, 60 minutes, 90 minutes, 3 hours, or even 4.5 hours or more at room temperature. In a specific example, a 4-HOOI complex dissolved in an aqueous solution maintains at least 97% purity for at least about 3 hours at room temperature.

In other examples, lyophilisates of disclosed complexes of 4-HOOI are more stable than a lyophilized preparation of 4-HOOI itself, for example, as the free peroxide. In some examples, the lyophilisate of the disclosed complexes have a longer shelf life than a lyophilized preparation of 4-HOOI itself, for example at least twice as long, such as at least five times as long.

As described above, in some examples, the disclosed lyophilisates further include an excipient, for example, a bulking agent, such as mannitol. In some examples, the lyophilisate includes a bulking agent selected from mannitol, anhydrous lactose, sucrose, D(+)-trehalose, dextran 40, and povidone (PVP K24). In certain examples, addition of such a bulking agent may improve the stability of the lyophilisate relative to the lyophilisate formulation in the absence of the bulking agent. In some examples, such a lyophilisate is stable at about −80° C., about −70° C., about −20° C., or even about 5° C., for example, over a period of one month, two months, three months, six months, nine months, one year, or even two years or more. In examples where the lyophilisate comprises a bulking agent, such as mannitol, the lyophilisate may include from about 1% to about 10%, or about 1% to about 5% (w/v) bulking agent, for example, mannitol.

The compounds disclosed herein may be administered orally, topically, transdermally, parenterally, via inhalation or spray and may be administered in dosage unit formulations containing conventional non-toxic pharmaceutically acceptable carriers, adjuvants and vehicles.

Typically, parenteral administration of the disclosed 4-HOOI complexes via injection is utilized. The 4-HOOI complexes may be provided in a single dose or chronically, dependent upon the particular disease, condition of the subject, toxicity of the compound, and other factors, as will be recognized by a person of ordinary skill in the art. The therapeutically effective amount of the compound or compounds administered can vary depending upon the desired effects and the factors noted above.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some examples, a disclosed compound is formulated as an oral dosage form, such as a pill, tablet, or capsule. Such oral dosage forms include at least one excipient, glidant, diluent, lubricant, and/or disintegrant. In some examples, suitable excipients, glidants, diluents, lubricants, and/or disintegrants include, but are not limited to, talc, fumed silicon dioxide, starch, calcium silicate, magnesium carbonate, magnesium oxide, magnesium lauryl sulfate, sodium lauryl sulfate, lactose, microcrystalline cellulose, hydroxypropylmethyl cellulose, dextrose, glucose, sucrose, starch, starch derivatives, calcium carbonate, dibasic calcium phosphate, magnesium carbonate, magnesium stearate, calcium stearate, sodium stearyl fumarate, polyethylene glycol 4000, polyethylene glycol 6000, sodium benzoate, light mineral oil, hydrogenated vegetable oils, stearic acid, glyceryl behenate, insoluble ion exchange resins, sodium starch glycolate, sodium carboxymethylcellulose (croscarmellose sodium), gums (e.g., agar, guar, xanthan), alginic acid, sodium alginate, and crospovidone.

In some examples, the oral dosage form comprises a compound as disclosed herein and at least one excipient, glidant, diluent, lubricant, and/or disintegrant; such as at least one excipient, glidant, diluent, lubricant, and/or disintegrant that is suitable for formulation with a hygroscopic active agent. In particular examples, the oral dosage form comprises at least one excipient, glidant, diluent, lubricant, and/or disintegrant selected from microcrystalline cellulose, lactose, sodium carboxymethylcellulose, magnesium stearate, dibasic calcium phosphate, sodium starch glycolate, hydroxypropylmethyl cellulose and mannitol.

In one example, a disclosed compound is formulated for administration to a mammalian subject (for example, a human subject). In one example, the pharmaceutical composition includes from about 0.1 mg/ml to about 250 mg/ml, such as from about 20 to about 100 mg/ml of a disclosed 4-HOOI complex (for example, 4-HOOI.Lys).

In particular examples, the disclosed pharmaceutical compositions are formulated into unit dosage forms. For example such unit dosage forms can contain from about 100 mg to about 1500 mg, such as from about 200 mg to about 1500 mg of a disclosed 4-HOOI complex (e.g., 4-HOOI.Lys) per dosage unit.

It is specifically contemplated in some embodiments that the present compounds are delivered via an injected and/or implanted drug depot, for instance comprising multi-vesicular liposomes such as in DepoFoam® (Pacira Pharmaceuticals, San Diego, Calif.) (see, for instance, Chamberlain et al. *Arch. Neuro.* 50: 261-264, 1993; Katri et al. *J. Pharm. Sci.* 87: 1341-1346, 1998; Ye et al., *J. Control Release* 64: 155-166, 2000; and Howell, *Cancer J.* 7: 219-227, 2001).

Methods are disclosed herein for treating conditions characterized by abnormal or pathological proliferative activity or neoplasia by administering one or more of the disclosed compounds and compositions to a subject. "Neoplasia" refers to the process of abnormal and uncontrolled cell growth. Neoplasia is one example of a proliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant."

Conditions that can be treated according to the disclosed methods include those characterized by abnormal cell growth and/or differentiation, such as cancers and other neoplastic conditions. Typical examples of proliferative disorders that can be treated using the disclosed compounds and compositions are listed below.

Examples of hematological tumors that can be treated using the compounds and compositions disclosed herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Additional examples of conditions that can be treated using the disclosed compounds and compositions include solid tumors, such as sarcomas and carcinomas, including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma or non-small cell lung carcinoma), ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, melanoma, and central nervous system (CNS) tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

In some examples, the compounds disclosed herein are superior to CPA or IFOS alone against CPA-resistant tumor growth. Therefore one aspect of a method disclosed herein includes treating a subject having a CPA-resistant neoplastic condition with a 4-HOOI complex disclosed herein.

In particular examples, the 4-HOOI complexes disclosed herein are administered to a subject having a central nervous system tumor (for example, a glioblastoma, astrocytoma, medulloblastoma, ependymoblastoma, or other CNS tumor). The CNS tumor may be a primary tumor or a metastatic tumor (including, but not limited to a metastasis of a breast cancer, lung cancer, melanoma, or other cancer). In some examples, the disclosed 4-HOOI complexes are able to pass through the blood-brain barrier and accumulate in the CNS. In particular examples, 4-HOOI accumulates in the CNS tumor, but does not accumulate in non-tumor CNS tissue.

In one example of the method a subject is administered from about 0.2 mg/kg/day to about 200 mg/kg/day of a disclosed 4-HOOI complex (such as 4-HOOI.Lys). For example, from about 0.5 to about 10 mg/kg/day, such as from about 1 to about 7.5 mg/kg/day of a disclosed compound can be administered to a subject. In another embodiment of the method a subject is administered from about 10 to about 700 mg/m$^2$/day, such as from about 30 to about 500 mg/m$^2$/day or from about 60 to about 200 mg/m$^2$/day. For example, from about 30 to about 200 mg/m$^2$/day, such as from about 40 to about 60 mg/m$^2$/day (for example about 30, 40, 50, 60, 70, 80, 90, 100, 110, 120, 130, 140, 150, 160, 170, 180, 190, or 200 mg/m$^2$/day) of a compound disclosed herein (such as 4-HOOI.Lys) is administered to a subject.

In some examples of the method for treating hyper-proliferative disorders (such as CNS tumors) disclosed herein, a disclosed compound or composition is administered to a subject on a multiple daily dosing schedule. In particular examples, the compound is administered on at least two days and on as many as five or more different days. In one aspect of multiple daily dosing schedules, the compound or composition is administered to the subject on consecutive days, such as from two to five consecutive days. When administered in multiple doses, the time period between each administration can vary and will depend in part on the subject being treated and the type of cancer being treated. In some examples, the disclosed compound is administered daily, bi-weekly, weekly, bi-monthly or monthly. When administered in multiple doses, the time period between each administration can vary and will depend in part on the subject being treated and the type of cancer being treated. One of skill in the art can determine an appropriate dosing schedule for each subject.

In some examples of the method, the disclosed compound or composition is administered to a subject in the absence of other therapeutic agents or treatments (such as additional anti-cancer therapeutics or radiation treatment).

In other examples of the method one or more additional therapeutic agents or treatments is administered to a subject in addition to the presently disclosed compounds and compositions. For example, additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors.

"Microtubule binding agent" refers to an agent that interacts with tubulin to stabilize or destabilize microtubule formation thereby inhibiting cell division. Examples of microtubule binding agents that can be used in conjunction with the presently disclosed 4-HOOI complexes include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art. For example, suitable epothilones and epothilone analogs for incorporation into the present compounds are described in International Publication No. WO 2004/018478, which is incorporated herein by reference. Taxoids, such as paclitaxel and docetaxel are currently believed to be particularly useful as therapeutic agents in the presently disclosed compounds. Examples of additional useful taxoids, including analogs of paclitaxel are taught by U.S. Pat. Nos. 6,610,860 to Holton, 5,530,020 to Gurram et al. and 5,912,264 to Wittman et al. Each of these patents is incorporated herein by reference.

Suitable DNA and/or RNA transcription regulators, including, without limitation, actinomycin D, daunorubicin, doxorubicin and derivatives and analogs thereof also are suitable for use in combination with the presently disclosed compounds.

DNA intercalators and cross-linking agents that can be utilized with the disclosed compounds include, without limitation, cisplatin, carboplatin, oxaliplatin, mitomycins, such as mitomycin C, bleomycin, chlorambucil, cyclophosphamide, penclomedine, and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors for use in combination with the presently disclosed compounds include, without limitation, camptothecin, etoposide, formestane, trichostatin and derivatives and analogs thereof.

Suitable therapeutics for use with the presently disclosed compounds that affect gene regulation include agents that result in increased or decreased expression of one or more genes, such as, without limitation, raloxifene, 5-azacytidine, 5-aza-2'-deoxycytidine, tamoxifen, 4-hydroxytamoxifen, mifepristone and derivatives and analogs thereof.

The term "angiogenesis inhibitor" is used herein, to mean a molecule including, but not limited to, biomolecules, such as peptides, proteins, enzymes, polysaccharides, oligonucleotides, DNA, RNA, recombinant vectors, and small molecules that function to inhibit blood vessel growth. Angiogenesis is implicated in certain pathological processes, such as those involved in disorders such as diabetic retinopathy, chronic inflammatory diseases, rheumatoid arthritis, dermatitis, psoriasis, stomach ulcers, and most types of human solid tumors.

Angiogenesis inhibitors are known in the art and examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof.

Other therapeutic agents, particularly anti-tumor agents, that may or may not fall under one or more of the classifications above, also are suitable for administration in combination with the presently disclosed compounds. By way of example, such agents include adriamycin, apigenin, rapamycin, zebularine, cimetidine, and derivatives and analogs thereof.

The disclosure is illustrated by the following non-limiting Examples.

Example 1

Synthesis and Properties of 4-HOOI.Lysine Complex

This example describes the synthesis of 4-HOOI and its lysine complex and the physical properties of the compounds.

Figure 1:
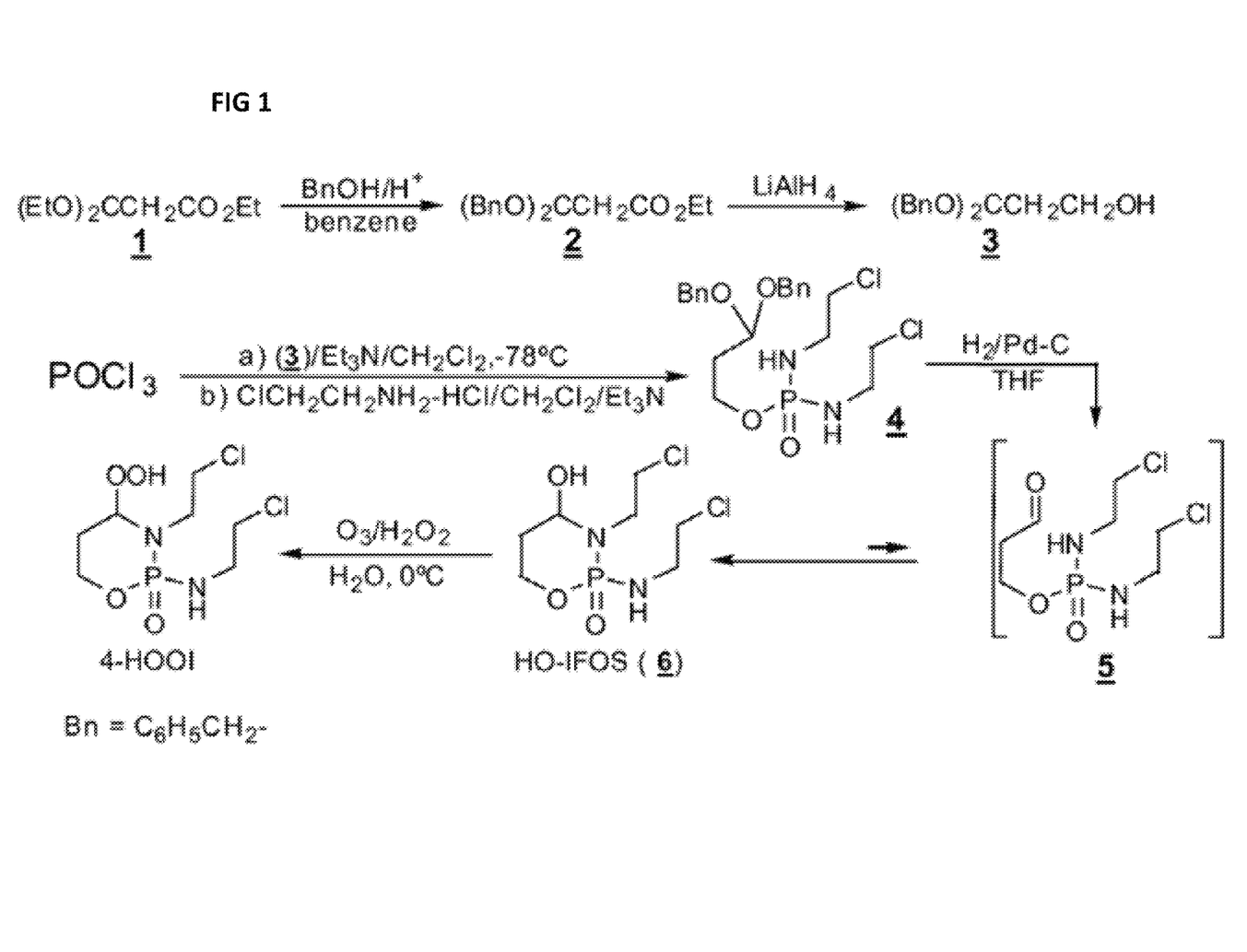
FIG. 1 is a schematic showing the synthesis of 4-HOOI

4-HOOI was produced as shown in FIG. 1. The overall yield for the synthesis was 43%, m.p. 123-124° C., with supporting NMR and MS data. 4-HOOI has a 2-chiral center, however, during recrystallization it will adapt to the most thermodynamically stable configuration, which is chair with the bulky substituent in the equatorial position.

4-HOOI was a white powder, m.p. 123-125° C., which was stable when stored dry at 4° C. The material was soluble in water, saline, chloroform, dichloromethane (DCM), ethanol, methanol, dimethylformamide (DMF), dimethyl sulfoxide (DMSO), and dimethylacetamide (DMA). A stock solution for assays was prepared in DMSO, DMA or acetonitrile at a concentration of 0.1 mg/ml and stored at −4° C.

Figure 2:
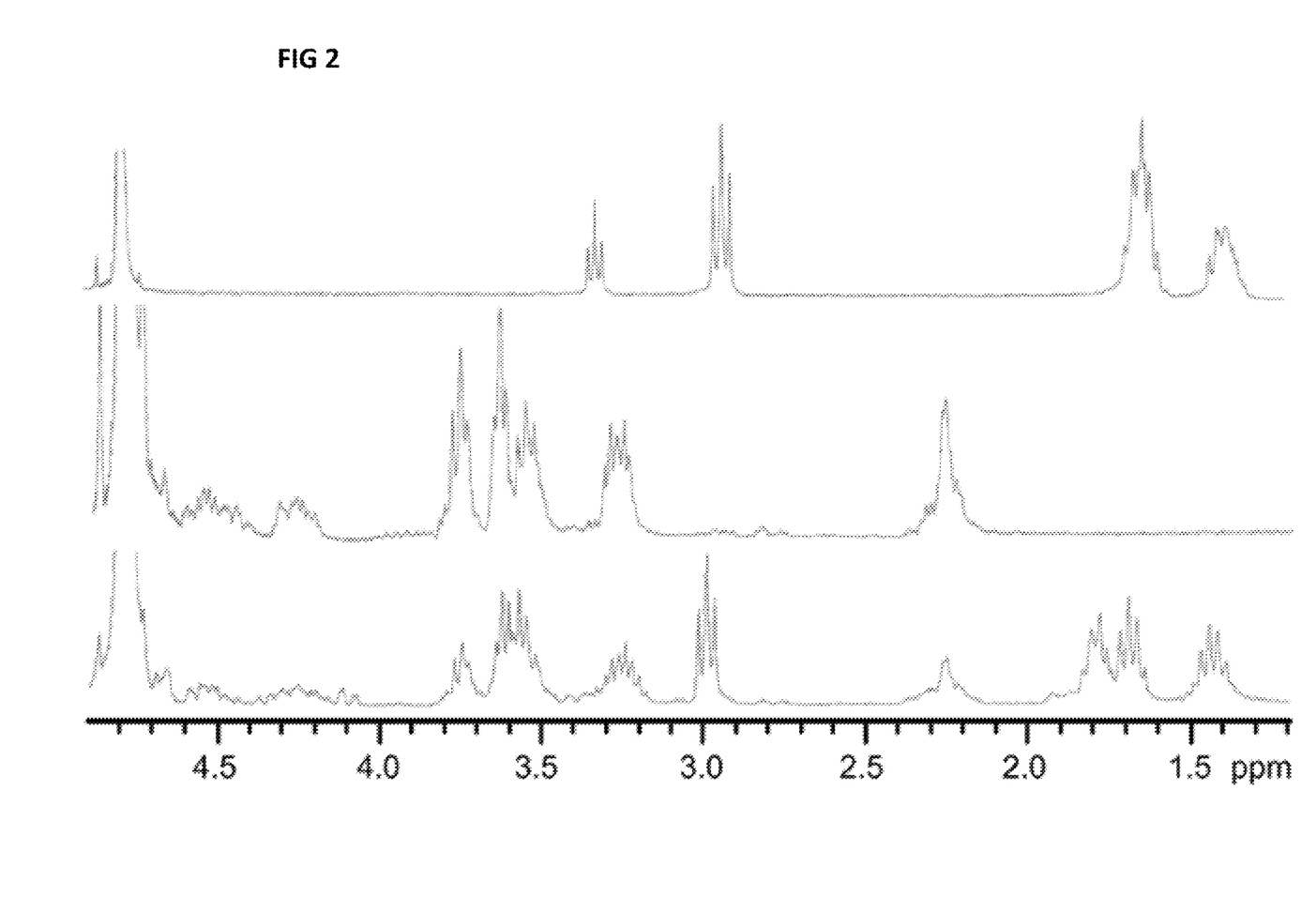
FIG. 2 is a series of $^1$H nuclear magnetic resonance (NMR) spectra (400 MHz, DMSO) of L-lysine (top), 4-HOOI (middle), and L-lysine.4-HOOI 2:1 (bottom) in water.
Figure 3:
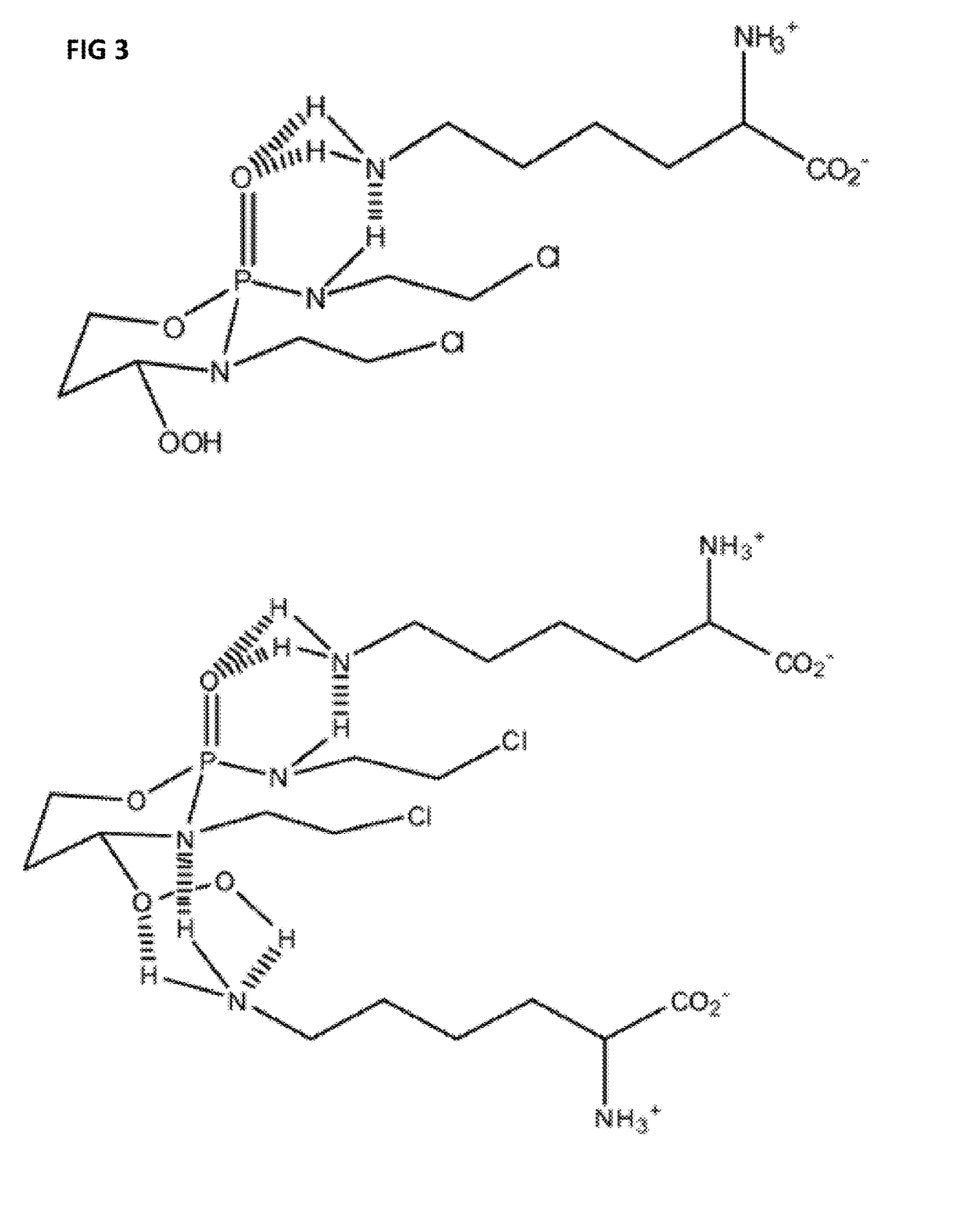
FIG. 3 is a pair of proposed structures for 4-HOOI.Lysine complexes. Top, proposed structure of a 1:1 4-HOOI.Lys complex; bottom, proposed structure of a 1:2 4-HOOI. Lys complex.

4-HOOI (0.5 mol in 125 mL of distilled water at 5° C.) was mixed with L-lysine (0.5 mol dissolved in 150 mL of distilled water at 5° C.). The solution was stirred for 30 minutes at 5° C., filtered, and the resultant solution lyophilized. Lyophilization was completed in 3 hours using a standard Ace glass evaporating system with the solution chilled to −75° C. 4-HOOI formed a stable complex with L-lysine, and no evidence of chemical reactions between the aldehydes intermediates and L-lysine were noted. The 1:1 4-HOOI.lysine complex was a white powder, dec.>275° C. without detonatation. The stability of 4-HOOI and 4-HOOI.lysine was monitored and was acceptable (Table 2). No reactions of the lysine and 4-HOOI to form an imine (Schiff base) or hydroxylamine were observed (FIG. 2). A 1:1 4-HOOI:lysine ratio was confirmed during lyophilization studies. Proposed structures for possible 4-HOOI.Lysine complexes are shown in FIG. 3.

HPLC Assays: The chromatographic equipment consisted of an Agilent 1200 delivery pump, a Rheodyne 7125 injector fitted with a 20 μl loop, an Agilent 1200 variable wavelength detector and an Agilent 3395 integrating recorder. The mobile phase was 0.9% saline with a flow rate of up to 1.5 ml/min. The column was an Alltech Econosphere ODS C-18, with 5 μm packing, dimensions 4.6 mm×30 cm. The assay included L-lysine as the internal standard and detection was at 195 nm wavelength. The resolution between the internal standard and the 4-HOOI exceeded baseline. With 0.9% saline as the mobile phase 4-HOOI produced a 9-11 minute peak area of $8 \times 10^6$ and with 30% acetonitrile mobile phase IFOS appeared at 14 minutes with peak area of $227 \times 10^6$.

GC/MS Assay: The stock solution of 4-HOOI was prepared in DMSO at a concentration of 0.1 mg/ml and stored at 0° C. 4-HOOI (100 μl of the stock solution) and 150 μl of t-butyl dimethylsilyl-N-methyl-trifluoroacetamide (TB-DMF) were added together in a tube. The mixture was then heated at 70° C. for five minutes and then allowed to stand for two hours at room temperature and frozen at −70° C. for later use as a standard.

To 100 μl of plasma containing 4-HOOI (75 ng/ml) in a glass centrifuge tube, 2 ml of cold dichloromethane was added and the mixture was vortexed for 1 minute (to allow protein precipitation). The tube was then frozen in a dry ice/acetone bath; the dichloromethane layer was removed and evaporated to dryness in vacuo. The residue was dissolved in 30 μl of DMA and 50 μl of TBDMF was added. The mixture was heated for five minutes at 70° C. and frozen or injected (2 or 3 μl) into a gas chromatograph coupled to a mass-spectrometer (Hewlett-Packard MS Engine). The column was an OV-1 and the oven temperature was at 180° C. at injection time that increased at 10° C. per minute to 250° C. with a helium flow rate of 1 ml per minute. The chromatogram of the pure compound had a unique peak at 15 minutes. Under these conditions, 4-HOOI quantification can be performed by selected ion monitoring (SIM) at m/z=406 amu (m=520−114) of fragments corresponding to mass spectrum of the t-butyldimethylsilyl derivatized compound—the loss of the well known dimethyl-t-butyl-Si group (m-114). The extraction efficacy was 85%.

P388 CPA-resistant murine leukemia cell line was injected intraperitoneally (IP). For IC implanted tumor cells, treatment was begun 5-7 days post-inoculation. For SC tumors, treatment was begun when the tumor was palpable (5-10 days post-inoculation). Mice were treated with the indicated dose of drug intraperitoneally once per day for 5 days. 4-HOOI was curative (84% LTS) for U251 glioblastoma implanted IC (Table 4). It should be noted that 4-demethylcholesteryloxy-carbonylpenclomedine (DM-CHOC-PEN), which is in clinical trials, only produced a 52% LTS in U251 glioblastoma (Morgan et al., *Cancer Chemother. Pharmacol* 64:829-835, 2009) and bis-chloronitrosourea (BCNU), which is the gold standard for the treatment of gliomas, only produced 72% ILS. No CNS/behavioral toxicity was noted for 4-HOOI.

TABLE 2

Stability Profile - Bulk 4-HOOI (DTI-01-7) vs. 4-HOOI•Lys (DTI-04-7)

| | | Batch | | | | |
|---|---|---|---|---|---|---|
| | DTI-01-7 | DTI-01-7/ *DTI-04-7 | DTI-01-7/ *DTI-04-7 | DTI-01-7/ *DTI-04-7 | DTI-01-7/ *DTI-04-7 | DTI-01-7/ *DTI-04-7 |
| Time | 0 | 0 | 2 months | 4 months | 6.5 months | 10 months |
| MP (° C.) | 123-125 | 122-124/*>275 | 123-125/*>275 | 123-125/*>275 | 123-125/*>275 | 123-125/*>275 |
| HPLC | >97% | >97% | >97% | >97% | >97% | >97% |
| NMR | Stable | Stable | Stable | Stable | Stable | Stable |
| Appearance | White crystals | White crystals/ *White powder | White crystals/ *White powder | White crystals/ *White powder | White crystals/ *White powder | White crystals |

Example 2

Anti-Tumor Activity of 4-HOOI

This example describes the anti-tumor activity of 4-HOOI utilizing in vitro and in vivo models.

4-HOOI and 4-HOOI.Lys were evaluated in vitro using 9 L rat glioma cells in culture. The $IC_{50}$ for each compound and also ifosfamide was determined (Table 3).

TABLE 3

4-HOOI Activity in vitro Against 9L Rat Glioma Cells

| Drug | Dose Range (μg/ml) | $IC_{50}$ (μg/ml) | Notes |
|---|---|---|---|
| 4-HOOI | 0.1-1.00 | 0.35 | Cell death about 6 hours post-exposure |
| 4-HOOI•Lys | 0.1-1.00 | >1.0 | Stabilized form prevented cell penetration |
| IFOS | 0.1-1.00 | >1.0 | Inactive without activation |

4-HOOI was screened in over 20 human xenograft tumor models and showed significantly improved antitumor activities compared to IFOS and IPM in breast cancer and glioma xenograft models and murine leukemia. 4-HOOI crossed the blood-brain barrier with no evidence of neurological or behavioral toxicity. Human breast cancer cell lines MX-1 and ZR75-1 were implanted subcutaneously (SC). Human glioblastoma cell line U251 was implanted intracranially (IC) and

TABLE 4

Response of Human Xenografts and Murine Tumors in vivo

| Drug | Dose (mg/kg/day) | # of Mice | MX-1 T-C (Days) | ZR-75-1 T-C (Days) | U251 T-C (Days) | P388/ CPA (% ILS) |
|---|---|---|---|---|---|---|
| 4-HOOI | 90 ($<LD_{10}$) | 10 | >28.8 (33% LTS) | >46.1 (83% CR) | +84 (1/5 CR) | +209* |
| IFOS | 40 (MTD) | 10 | 8.6 (No LTS) | >43.8 (17% CR) | 50 (0/5 CR) | +42 |
| IPM | 40 (MTD) | 10 | 2.1 | NA | NA | +85 |
| BCNU | 15 (MTD) | 5 | NA | NA | +84 (0/5 CR) | NA |
| TMZ | 120 mg (MTD) | 5 | NA | NA | +84 (1/5 CR) | NA |

*6-log cell kill
T-C (days) = difference in median time post-implant for tumors of treated groups to attain an evaluation size compared to median of control group
MTD = maximum tolerated dose
LTS = long term survivors
CR = complete response
ILS = increased length of survival 4-HOOI was tested against a number of additional solid tumor xenografts and leukemias. 4-HOOI was curative (upon treatment at its $LD_{10}$ dose) in murine L1210 and P388 leukemias and murine solid tumors, including Lewis lung carcinoma, Ridgway osteogenic sarcoma (ROS), and ependymoblastoma EP37, showing 25-50% T/C delay values (Tables 5 and 6).

TABLE 5

Activity of 4-HOOI and IFOS (MTD) Against Human Solid Tumor Xenografts

| Tumor Type | 4-HOOI T-C (Days Delay) | IFOS T-C (Days Delay) |
|---|---|---|
| NCI-H69 Small cell lung carcinoma (sc) | 9.1 | 6.2 |
| NCI-H23 Non-small cell lung carcinoma (sc) | 10.9 | 13.7 |
| OVCAR-3 Ovarian (sc) | 14.2 | 12.4 |
| SAOS-2 Osteosarcoma (sc) | 58.3 | >61.9 |
| SK-MEL-31 Melanoma (sc) | 5.7 | 10.9 | sc; subcutaneous implant; treatment route: intraperitoneal

TABLE 6

Activity of 4-HOOI Against Experimental Tumors

| Tumor | Implant Site | Implant Size | Dose (mg/kg) | Schedule | Route | Survivors | T/C (%) |
|---|---|---|---|---|---|---|---|
| L1210 leukemia | IP | $10^5$ cells | 75 | Single dose | IP | 4/6 | 276 |
| P388 leukemia | IP | $10^7$ cells | 175 | Single dose | IP | 7/9 | 612 |
| Lewis lung | SC | $10^6$ cells | 155 | Single dose | IP | 8/9 | 391 |
| Ridgway/sarcoma | SC | 30 mg fragment | 150 | Q14d x 3 | IP | 4/10 | 364 |
| Ridgway/CPA | SC | 30 mg fragment | 150 | Q14d x 3 | IP | 1/10 | 268 |
| Ependymoblastoma | SC | $10^5$ cells | 240 | Single dose | IP | 0/10 | 150 |
| Ependymoblastoma | SC | 30 mg fragment | 240 | Single dose | IP | 1/10 | 125 |

The activity of 4-HOOI and 4-HOOI.Lys were also evaluated in vivo against glioma. Rat glioma 9 L cells ($10^6$ cells) were implanted subcutaneously in female Hsd:SD rats. Eight days post-implantation, 4-HOOI, 4-HOOI.Lys, or IFOS was administered once intraperitoneally. Temozolomide (TMZ) was administered orally three times, four days apart. The rats were followed for 54 days. 4-HOOI and 4-HOOI.Lys were both effective in increasing survival of the animals (Table 7). No hematuria was observed in animals treated with 4-HOOI or 4-HOOI.Lys, but was observed in animals treated with IFOS. No weight loss was observed in animals treated with 4-HOOI or 4-HOOI.Lys and no toxicity was observed with the two-drug combination. Long term survival was greater with 4-HOOI.Lys than with 4-HOOI (100% vs. 89%).

TABLE 7

Activity of 4-HOOI Against 9L Rat Glioma

| Drug | Dose (mg/kg) | Life Span (% ILS) | Long Term Survival (% LTS) |
|---|---|---|---|
| Control | Vehicle | 0 | 0/9 |
| 4-HOOI | 100 | +54 | 89% (8/9 CR) |
| 4-HOOI•Lys | 125 | +54 | 100% (9/9 CR) |
| IFOS | 400 | 5 | 0 |
| TMZ | 120 | +54 | 60% (3/5 CR) |
| 4-HOOI•Lys/TMZ | 75/75 | +54 | 80% (4/5 CR) |

Example 3

In Vivo Toxicology and Pharmacology

This example describes animal toxicology studies in mice, rats, and dogs, used to determine $LD_{10}$ and $LD_{50}$ values and to evaluate the production of chloroacetaldehyde (CAA) and acrolein (ACR).

A single (1-day) dosing schedule was selected based on the pharmacology of the maximum tolerated dose (MTD) and toxicology of 4-HOOI at 100 mg/kg per day dosing (dose limiting toxicity (DLT) and mouse death ($LD_{10}$) occurred at 200 mg/kg). Specific emphasis was placed on documenting potential toxicities associated with IV administered peroxides, namely convulsions, hemolysis, arterial gas emboli-pulmonary damage, and neurological pathology.

Mouse IV Dosing: Single IV mouse-dosing studies calculated a $LD_{10/50}$ of 200/385 mg/kg (both sexes; with 95% confidence limits). No central nervous system toxicity was noted in the animal studies at 100 or 200 mg/kg. Non-life threatening myelosuppression was the DLT in mice at 100 mg/kg after a single IV dose. The $LD_{10}$ was 200 mg/kg for a single dose and 180 mg/kg for single doses given once per day for 5 days. Ranges of dosing were 60-400 mg/kg. No convulsions, neuropathies or renal dysfunctions or deaths were noted at doses of <200 mg/kg. Animals were monitored for 14 days post treatment.

Rat Dosing: Neuro-oncology studies with 4-HOOI were conducted to evaluate the product as compared to ifosfamide in a rat neurobehavioral modified Morris water maze. Ifosfamide produces coma and neuro-edema in high doses. Adult Sprague Dawley female rats (160-180 g) in groups of 3-6 rats per dosing were treated IP with a single dose of IFOS (400 mg/kg), 4-HOOI (200 mg/kg), or 4-HOOI.Lys (300 mg/kg) and monitored with timing to find a stage covered with peanuts in a 8 cm deep pool (36×48 cm) of water. Timings (six at each time) were measured at 1, 2, 3, and 20 hours post-dosing to monitor learning and memory. There were no significant differences between controls, 4-HOOI, and 4-HOOI.Lys in the memory and learning time intervals. The IFOS treated animals had shakes and tremors, but demonstrated normal learning behavioral patterns. Five days later, all rats treated with IFOS demonstrated hemorrhagic cystitis with gross bleeding, and bone marrow evaluations revealed pancytopenia. 4-HOOI and 4-HOOI.Lys treated animals did not reveal hemorrhagic cystitis, renal tubular necrosis, or bone marrow depletion. Histological examinations confirmed the gross observations.

Non-Rodent (Dog) Toxicology with 1-Day Intravenous Dosing: This study evaluated the acute toxicity of 4-HOOI in beagle dogs following a single intravenous dose with observation for 14 days. During this period, dogs were observed for clinical signs of toxicity at 1 and 4 hours post-dose on day 1, twice daily on days 2-14, and necropsied on day 15. In addition, daily body weights were recorded prior to treatment. Complete gross/histological pathology, complete blood chemistry, and hematology were evaluated on all animals dying on study or necropsied at study termination. Appropriate $LD_{10/50}$ values were calculated.

Figure 4:
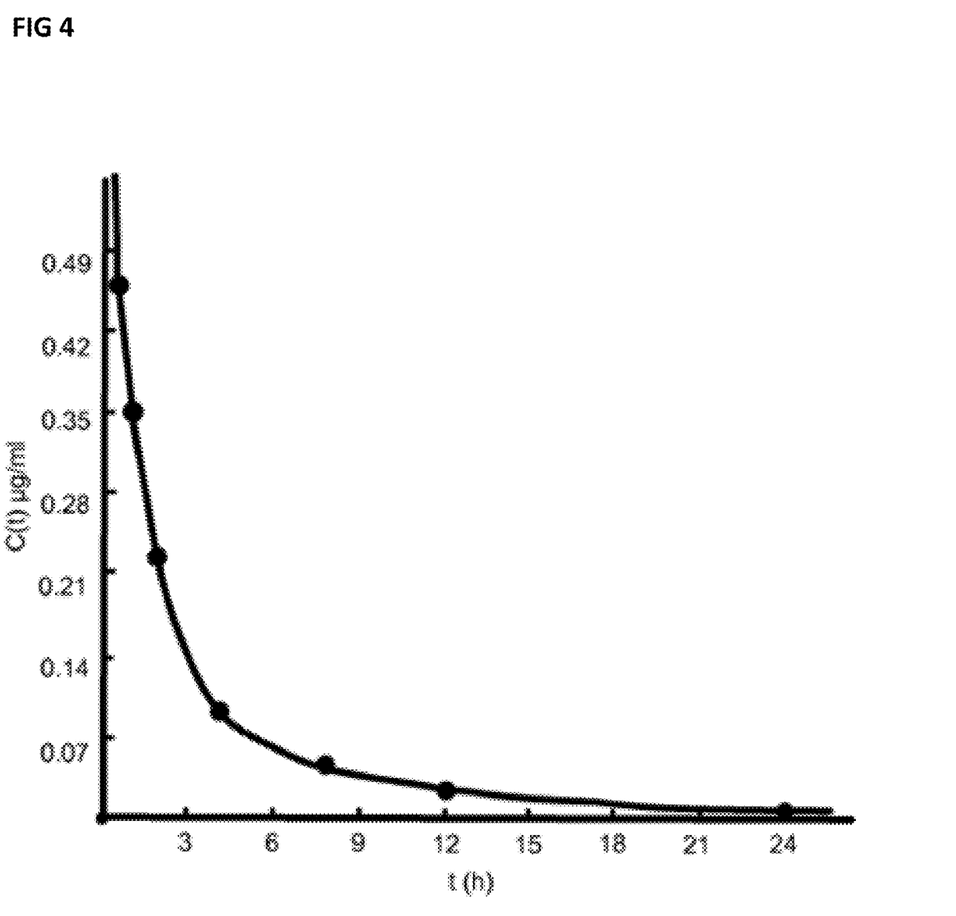
FIG. 4 is a bioavailability curve for a dog dosed intravenously with 30 mg/kg 4-HOOI. Plasma 4-HOOI was assayed by GC/MS.

4-HOOI was administered as a slow bolus injection once to pairs of male dogs at escalating doses of 10, 15, 20, and 30 mg/kg. Animals were anesthetized with ketamine during the administration of drug. Blood was drawn and plasma was separated and stored at −70° C. Complete chemistry, hematology, and urine analysis were obtained prior to dosing, 3-days post and 14-days post dosing. Bioavailability for one dog dosed with 30 mg/kg is shown in FIG. 4. Overall, pharmacokinetics values in dogs revealed the following profile for 30 mg/kg: $AUC_{0-t}$=1.53 mg h/L; $T_{1/2}\alpha$=0.93 h; $T_{1/2}\beta$=6.1 h; and CL=19.5 L/h (a two compartment model). Pharmacokinetics appeared linear. The AUC was linear for 10 and 30 mg/kg doses.

Daily exams were made and upon termination. All of the 20 and 30 mg/kg dosed animals required euthanization by day 8 due to deteriorating physical conditions, including loss of appetite and weight loss. Bone marrow and spleen depletion were key organs probably associated with the animals' demise. No kidney or renal system pathology was noted. This is in contrast to IPM where renal tubular necrosis was dose limiting in humans. No CNS pathology was noted. All of the 10 and 15 mg/kg dosed animals survived and at 15 days there was improving bone marrow, however spleens were still depleted. One 15 mg/kg dosed animal displayed a small thyroid. Based on the results and outcomes of this study, the $LD_{10}$ was calculated to be 17.24 mg/kg, while the $LD_{50}$ was calculated to be 17.32 mg/kg.

Plasma Levels of 4-HOOI, CAA and ACR: Adult female C3H mice were treated with CPA (250 mg/kg), IFOS (400 mg/kg) or 4-HOOI (100 mg/kg) as single agents by IV injection and blood was collected and measured for 4-HOOI, CAA, and ACR. Half of each plasma sample was lyophilized to collect ACR in a dry ice/methanol-cooled trap. The lyophilisate was treated with pentafluorophenylhydrazine, saturated with NaCl, extracted with ethyl acetate, and measured by GC/MS with selective ion monitoring or HPLC (4.4 mins, mobile phase 70% acetonitrile at 254 nm). For chloroacetaldehyde, the other half of the plasma sample was treated directly with the above trapping agent and the same procedure was used (6 mins) compared with synthetic controls.

4-HOOI did not generate any detectable plasma levels of CAA in mice, in contrast to IFOS (Table 8). There was a trace amount of CAA seen at 120 in the dog. The highest tolerated single IV dose tolerated for IFOS was 400 mg/kg and for 4-HOOI was 100 mg/kg. Acrolein plasma levels obtained from animals receiving 4-HOOI (100 mg/kg) are shown in Table 8. ACR plasma levels were lower for 4-HOOI in both mice and dog. AUC values (0-120 mg-min/ml) for acrolein using the trapezoidal rule were as follows: CPA: 1520; IFOS: 960; 4-HOOI: 500. Neither mice nor dogs dosed with 4-HHOI demonstrated urinary hemorrhagic cystitis, in contrast to the IFOS treated mice, in which the pathology occurred at day 5 post dosing.

TABLE 8

Chloroacetaldehyde (CAA) and Acrolein (ACR) Plasma Levels in Mice

| | Time post-infusion | | | | | | | | | |
|---|---|---|---|---|---|---|---|---|---|---|
| | 15 minutes | | 30 minutes | | 60 minutes | | 120 minutes | | 240 minutes | |
| Agent (dose) | CAA | ACR | CAA | ACR | CAA | ACR | CAA | ACR | CAA | ACR |
| CPA (250 mg/kg) | 2.0 | 9.3 | 3.4 | 9.7 | 7.1 | 18.8 | 6.1 | 9.9 | NA | NA |
| IFOS (400 mg/kg) | 1.0 | 7.4 | 1.4 | 5.4 | 2.1 | 10.2 | 0 | 8.7 | NA | NA |
| 4-HOOI (100 mg/kg) | 0 | 6.6 | 0 | 4.1 | 0 | 4.9 | 0 | 2.3 | NA | NA |
| 4-HOOI (30 mg/kg)* | NA | NA | 0 | 0.9 | 0 | 3.7 | 0.27 | 4.9 | 0 | 3.0 |

Levels of CAA and ACR are µg/ml plasma
*Data from dogs administered a single IV bolus The experimental anti-tumor activity of 4-HOOI as compared to IPM and IFOS suggested that 4-HOOI was more active than the other two agents against several tumor types (Tables 4-6) and less toxic, secondary to not generating any detectable plasma chloroacetaldehyde and less acrolein (Table 8). 4-HOOI is a pro-drug for IPM, but does not produce renal tubular necrosis as seen with the latter and is more active against some tumor types Table 4).

Example 4

Central Nervous System Accumulation of 4-HOOI

Female athymic NCr-nu/nu mice were intracranially implanted with U251 glioma cells and divided into controls (n=5) and treated: 4-HOOI (n=5) or TMZ (n=5). Mice were administered 4-HOOI (135 mg/kg/day) in saline IP daily for two consecutive days beginning 4 days post-inoculation of glioma ells. TMZ (120 mg/kg×2 days) was administered by oral gavage. Four hours after the second treatment of each group of animals, they were sacrificed and the brains removed intact and flash frozen in liquid nitrogen. The intact frozen brains (about 1.3 g) were coronal sliced into three sections in a mouse brain blocker (Kopf, Tujunga, Calif.). The encapsulated gliomas were easily identified and separated from normal brain with a scalpel. Complete separations were verified using a microscopic "touch finger print" technique.

The tumor tissues were weighed, pooled and homogenized in 10 ml 0.6 M phosphate buffer, pH 7.4 at 5° C. This process was repeated for the normal (non-tumor) brain tissues. The cold homogenates were extracted with 10 ml chloroform and the organic layer was separated and evaporated to dryness. Preparative TLC on silica gel plates followed by HPLC revealed 4-HOOI ($R_f$ 0.74) at 100-126 ng/g glioma tissue. No drug was identified in the normal brain tissue. The five control mice bearing IC implanted U251 cells (but not treated) were used as the dissection and extraction models. No chemicals or substances that could have interfered with the above extraction assay were noted in these mice. This indicates that 4-HOOI is able to cross the blood-brain barrier and is selectively accumulated by tumor tissue.

Example 5

Preparation of 4-HOOI.Lys Lyophilisate

L-lysine (non-animal origin) is dissolved in chilled water (2-8° C.) and 4-HOOI is slowly added (1:1 ratio) with stirring until all the solid material is dissolved. The solution is filtered through 0.22-micron sterile filters, dispensed into vials (500 mg per vial) and flash lyophilized at −45° C. The vials are sealed under nitrogen at 5° C. with metal caps/rubber centers.

Example 6

Clinical Trial in Cancer Patients

This example describes methods for evaluating 4-HOOI as a treatment with advanced or recurrent cancer, including determining the maximum tolerated dose and evaluating any associated toxicities.

Manufacture of Lyophilized 4-HOOI.Lys (clinical product): Lyophilized sterile 4-HOOI.Lys is prepared under FDA approved c-GMP guidelines. The process involves dissolving 4-HOOI (20 g) in 0.9% saline, and adding 22 g L-lysine (Sigma Aldrich, St. Louis, Mo.), filtering through microbial filters and lyophilizing in vials to contain 500 mg of 4-HOOI.Lys per vial with closure under nitrogen at 5° C. The product is prepared such that the 4-HOOI.Lys may be redissolved in saline or water, in situ, in each vial just prior to use.

Patient Selection: Patients with histologically documented solid malignancies refractory to conventional therapy, or for which no effective therapy exists are candidates for the study and must meet eligibility criteria. Enrollment of patients with metastatic CNS lesions and/or glioblastoma is encouraged. Laboratory and blood drawing schedules are outlined in Table 11 (below). All patients are required to sign an institutional review board-approved informed consent.

A. Eligibility Criteria

Inclusion Criteria: Patients must meet all of the following criteria to be enrolled in the study: 1) histological proof of advanced, unresectable cancer; 2) Karnofsky performance status of equal to or greater than 70; 3) written informed consent indicating that they are aware of the investigational nature of this study; 4) stable peripheral CBC: WBC≧4000 mm$^3$ and platelet counts≧100,000 mm$^3$; 5) no major surgery within 14 days; no wide field radiotherapy and/or chemotherapy within 28 days; no nitrosourea/mitomycin within 6 weeks of entering the study; 6) stable hepatic and renal functions with AST and ALT<2.5×ULN and creatinine<1.5× ULN, respectively.

Exclusion Criteria: Any of the following conditions will exclude a patient from enrollment in the study: 1) leukemia; 2) active uncontrolled infections; 3) any evidence of uncontrolled pulmonary/cardiovascular disease; 4) history of neuropsychiatric disorders; 5) severe unstable diabetes mellitus; 6) coagulopathies or thromboembolic disease; 7) any other medical condition which renders the patient unable to complete the study (a life expectancy <10 weeks) or which would interfere with optimal participation into the study or produce significant risk; 8) females of childbearing potential not using one of the following birth control methods: oral, implantable, injectable contraceptives or abstinence; 9) male patients having sexual relations with women of child bearing potential that do not use condoms; 10) pregnant or lactating females. All patients or legal representatives must give written informed consent according to institutional/federal guidelines before treatment.

B. Study Design—Open Label Phase I

A single dose schedule is supported by the mouse toxicity data. In the present study, the initial dose (dose level 1) is 40-60 mg/m$^2$. This is about ⅒ of the $LD_{10}$ from the mouse single IV dose toxicity studies (Example 3). The lyophilized 4-HOOI.Lys is dissolved in 50 ml saline and infused over 1 hour. Treatments are repeated once every three weeks (providing laboratory values are acceptable). The dose escalation/de-escalation rules are based on definitions of dose-limiting toxicity (DLT) and of "moderate" toxicity. Children are admitted to the hospital for the initial infusion.

Dose Limiting Toxicity (DLT) is graded according to the National Cancer Institute Common Toxicity Criteria Version 3.0. DLT are defined as: hematological toxicity: (a) leukocytes, grade IV (WBC<1000/mm$^3$); neutrophils/granulocytes, grade IV (ANC/AGC<500/mm$^3$) lasting at least 7 days +/− fever or grade 3-4 sepsis; (b) platelets 10,000-25,000/mm$^3$ lasting at least 7 days or of any duration associated with grade 3-4 hemorrhage, or platelets <10,000/mm$^3$ for any duration; (c) hemoglobin, grade IV, (<6.5 g/dl), when it cannot be treated with transfusions. Non-hematological toxicity: ≧grade III, (a) except for nausea and/or vomiting in the absence of appropriate anti-emetic regimens; (b) grade II encephalopathy with MRI correlate; (c) all anaphylactic reactions. All other types of toxicity are considered dose limiting, when they reach grade III (NCI CTCAE v3.0), except for hair loss. Maximum tolerated dose (MTD) is defined as the highest dose at which no more than 1 of 6 patients developed a DLT.

The Phase 1 trial follows the standard 3+3 design. The study is divided into a 3-patient cohort phase and then a standard 3-6 patient cohort phase. During the early phase, there are 3 patients entered per cohort and the dose for each patient is the initial dose described or the previous level dose plus 100%. When the first DLT occurs, the 3-cohort patient number dose is expanded to a minimum of 6 patients. If ⅓ experience first course DLT, up to 3 more patients are started at that same dose level. If 2 or more experience first course DLT, no further patients are started at that dose. This study design is summarized in Tables 9 and 10.

TABLE 9

Patient Number Rule

| Number of Patients with DLT at Given Dose Level | Number of Patients per Cohort |
|---|---|
| Initial dose-3 patients; if 0 out of 3 | Then enter 3 patients at the next higher dose level |
| if 1 out of 3 | Then enter at least 3 more patients (total 6) at this dose level |
| if ≧2 out of 3 | DLT: ≧2 out of 6-dose escalation will be stopped. This dose level will be declared the maximally administered dose (highest dose administered)* If the previous dose level had 6 patients, then the study is completed and no further patients will be enrolled. If the previous dose level had only 3 patients, add 3 more to the previous cohort of 3 at the previous (lower) dose level (rule out missing a DLT). |

TABLE 9-continued

Patient Number Rule

| Number of Patients with DLT at Given Dose Level | Number of Patients per Cohort |
|---|---|
| ≦1 out of 6 | Then proceed to the next higher dose level If the next (higher) dose level has been tested and had ≧2 DLT, then the study is completed and no further patients will be enrolled. This is the recommended dose. If the next (higher) dose level was not tested yet, then proceed to next dose level, enter 3 additional patients on next higher dose level before enrolling 6 patients. |
| ≧2 out of 6 | Dose escalation will be stopped. This dose level will be declared the maximally administered dose (highest dose administered)* If the previous dose level had 6 patients, then the study is completed and no further patients will be enrolled. If the previous dose level had only 3 patients, add 3 more to the previous cohort of 3 at the previous (lower) dose level (rule out missing a DLT). then the study is completed |

*Recommended phase 2 dose-maximum tolerated dose level that produces a DLT ≦1 in 6 pts.-the level below the maximally administered dose. At least 6 pts will be entered at this dose.

TABLE 10

Escalation Drug Dose Rule

| Maximal Toxicity Observed | Drug Dose to be Given to a Cohort |
|---|---|
| ≦1 patient with Grade I toxicity | Next dose level = previous dose level + 100% of dose level 1* |
| ≧1 patients with Grade II toxicity and no Grade III/IV toxicity | Next dose level = previous dose level + 50% of dose level 1* |
| 1 patient with Grade III/IV toxicity that dose not meet DLT criteria | Next dose level = previous dose level + 25% of dose level 1* Cohort should be expanded to 6 or study completed |
| Two or more patients with DLT | No further dose escalation |

*Dose level 1 = 60 mg/m$^2$

A minimum of 2 courses is required for a patient to be considered as having received an adequate trial to evaluate efficacy. A course is defined as days of therapy plus the required observation until the time for the next treatment. All patients are evaluated for toxicity and response (Table 11). After four courses of treatment, patients are off all therapy unless they are in complete remission, have minimal residual disease, or have at least responded partially to the treatments since start of the protocol. Patients who experience partial or complete remission while being treated may continue to receive the drug, and those patients with complete tumor remission may continue on the drug once every 3 weeks for a total of one year.

TABLE 11

Follow-up Evaluation

| | | | | Off-Study Follow-up | |
|---|---|---|---|---|---|
| Test | Pre-Treatment | Weekly | Every 2 Cycles | 3 Weeks off study | Every 3 months |
| Physical/vital signs | X | X | | X | X |
| Measurement of lesion (when possible) | X | | X | X | X |
| Weight | X | X | | X | X |
| X-rays/scans | X | | X | X | X |
| EKG | X | | X | X | X |
| CBC, diff, platelets | X | X | | X | X |
| CMP | X | X | | X | X |
| Urinalysis | X | X | | X | X |
| PK studies* | | | | | |

*PK studies will be conducted on the day of treatment and subsequent days per protocol.

Individual dose escalation is allowed. Patients who began at one level will continue at that level for at least 2 courses to observe cumulative toxicity. In the absence of toxicity, they may move on to the next dose level as soon as the whole study has moved on to the next level. Exceptions from requirement of a second cycle at the past lower dose are permitted if by then the study center has received data indicating a lack of toxicity at the next level, and has moved on to the following level (two levels higher). This is the case when three previously untreated patients have been treated at a higher dose level, are fully evaluable and no toxicity has been noted. Dose escalation is not allowed beyond the MAD, if the study has established the DLT, even if the individual has not yet experienced toxicity.

Individual dose reduction is mandatory in case of toxicity. Dose is adjusted to toxicity other than hematological toxicity as follows: Grade 0 or 1—same dose; Grade 2—decrease by 30% of given dose; Grade 3—decrease by 50% of given dose and investigator should be informed; Grade 4—investigator must be consulted and drug stopped.

Repeated courses are administered at 3 week intervals when: WBC≧4,000 mm$^3$; platelets>100,000 mm$^3$; chemistry parameters must return to pre-treatment values. All patients are evaluated for toxicity; if any occurs at the initial low dosage, the escalation is rescheduled.

If patients demonstrate increasing disease, experience unacceptable or life threatening side effects or toxicities, they are removed from the study. If no toxicities and/or unacceptable side effects are noted, and a response is noted, the patients may remain on therapy and may be considered for escalated treatment schedules until they relapse or become toxic. Repeat courses are in three week intervals. After four courses of treatment, patients will be off all therapy unless they have responded to the treatments.

Patients are removed from the study after one or more courses of chemotherapy when any of the following are noted: 1) increasing disease; 2) qualitatively unacceptable toxicity; 3) life threatening toxicity and/or 4) patients who are unable to comply with protocol requirements.

Any adverse event encountered during the study is evaluated according to the CTCAE v3.0 grading system (0-4). The duration and treatment of all adverse events are to be recorded. A complete examination, including vital signs, weight, hematology, CMP, and urinalysis is performed when an adverse event is noted.

All lesions are described and measured on enrollment, every two cycles while on therapy, and at the end of the study. The ability of 4-HOOI to induce a regression in the size(s) of measurable lesions is monitored (complete response, disappearance of all detectable lesions for at least 4-weeks; partial response, ≧50% decrease in the sum of the products of two perpendicular diameters of the index lesion(s) and no new lesions for at least 4-weeks; stable disease or no change, ≦50% change for at least 4 weeks; progressive disease, >25% increase in size(s) of lesions).

All patients are available for bioavailability studies provided: 1) that they consent to such studies; 2) that they have adequate venous access for repeated blood sampling; and 3) that they can be available for multiple drug samplings after treatment. One to two patients are evaluated at each dose level. For pharmacokinetic studies, 1.5-2 ml of blood (heparin tube) is collected for each sample. Samples are centrifuged immediately and the plasma separated and frozen immediately. Baseline samples (−5 min and 0 times) are collected before the drug is administered. Samples are then collected at 5, 15, 30, and 60 minutes after treatment, then at 2, 4, 8, 24, 36, and 48 hours after drug administration. Blood samples are centrifuged at 1000 g for 10 min at room temperature immediately after sampling, the plasma removed and stored at −70° C. until assayed. The bioavailability profile parameters for 4-HOOI and identified metabolites are determined, including AUC, CL, $T_{max}$, Vd, $T_{1/2\beta}$, and $C_{max}$.

In view of the many possible embodiments to which the principles of the disclosure may be applied, it should be recognized that the illustrated embodiments are only examples and should not be taken as limiting the scope of the invention. Rather, the scope of the invention is defined by the following claims. I therefore claim as my invention all that comes within the scope and spirit of these claims.

I claim:
1. A compound of the formula:

wherein A represents an ammonium species selected from the conjugate acid of a basic amino acid selected from lysine, arginine, histidine, homolysine, homoarginine, and ornithine; quaternary ammonium; aliphatic ammonium; heterocyclic ammonium; aromatic ammonium; substituted and unsubstituted pyridinium; guanidinium; and amidinium; and wherein X and Y independently represent leaving groups.

2. The compound of claim 1, wherein A is the conjugate acid of a basic amino acid.

3. The compound of claim 1, wherein A represents $BH^+$ and B is an amine selected from the basic amino acids, cyclohexylamine, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine.

4. The compound of claim 3, wherein B is a basic amino acid selected from lysine, homolysine, arginine, homoarginine, histidine, ornithine, and combinations or two or more thereof.

5. The compound of claim 4, wherein B is lysine.

6. The compound of claim 1, wherein X and Y independently are selected from the halogens and the sulfonates.

7. The compound of claim 6, wherein X and Y are halogen.

8. The compound of claim 7, wherein X and Y are chlorine.

9. A pharmaceutical composition comprising the compound of claim 1 and a pharmaceutically acceptable carrier.

10. The pharmaceutical composition of claim 9, wherein the composition comprises a solution formulated for administration to a human subject.

11. The pharmaceutical composition of claim 10, wherein the solution comprises from about 0.1 mg/ml to about 250 mg/ml of the compound.

12. A complex comprising a 4-hydroperoxy ifosfamide anion and an ammonium cation.

13. The complex of claim 12, further comprising a second amine or ammonium cation.

14. The complex of claim 13, wherein the ammonium cation is a conjugate acid of lysine or tris(hydroxymethyl)methylamine.

15. A pharmaceutical composition comprising the complex of claim 12 and a pharmaceutically acceptable carrier.

16. The pharmaceutical composition of claim 15, wherein the composition comprises at least two equivalents of amine base per equivalent of 4-hydroperoxy ifosfamide.

17. A method of treating a subject with cancer, comprising administering a therapeutically effective amount of the pharmaceutical composition of claim 9 to the subject having cancer, wherein the composition comprises a therapeutically effective amount of the compound.

18. The method of claim 17, wherein the subject has a central nervous system cancer, breast cancer, bone cancer, lung cancer, melanoma, ovarian cancer or leukemia.

19. The method of claim 17, comprising administering from about 10 mg/m²/day to about 700 mg/m²/day of the compound to the subject.

20. The method of claim 18, wherein the subject has a central nervous system cancer comprising glioblastoma, astrocytoma, oligodendroglioma, or ependymoblastoma.

21. The method of claim 20, wherein the central nervous system cancer comprises a primary brain cancer or a metastatic brain cancer.

22. A lyophilisate comprising 4-hydroperoxy ifosfamide, having a structure of formula:

wherein A represents an ammonium species selected from the conjugate acid of a basic amino acid, quaternary ammonium, aliphatic ammonium, heterocyclic ammonium, aromatic ammonium, substituted and unsubstituted pyridinium, guanidinium, and amidinium; and wherein X and Y independently represent leaving groups.

23. The lyophilisate of claim 22, wherein X and Y are chloride.

24. The lyophilisate of claim 22, wherein the basic amino acid is lysine.

25. The lyophilisate of claim 22, further comprising an excipient.

* * * * *